(12) United States Patent
Sakai et al.

(10) Patent No.: US 11,110,204 B2
(45) Date of Patent: Sep. 7, 2021

(54) METHOD OF PRODUCING BIOABSORBABLE MEMBRANE

(71) Applicant: GC Corporation, Shizuoka (JP)

(72) Inventors: Yuuhiro Sakai, Tokyo (JP); Yusuke Shigemitsu, Tokyo (JP); Kyohei Toyonaga, Tokyo (JP); Hidetoshi Funabashi, Tokyo (JP)

(73) Assignee: GC Corporation, Shizuoka (JP)

(*) Notice: Subject to any disclaimer, the term of this patent is extended or adjusted under 35 U.S.C. 154(b) by 136 days.

(21) Appl. No.: 16/336,622

(22) PCT Filed: Jun. 2, 2017

(86) PCT No.: PCT/JP2017/020592
§ 371 (c)(1),
(2) Date: Mar. 26, 2019

(87) PCT Pub. No.: WO2018/061323
PCT Pub. Date: Apr. 5, 2018

(65) Prior Publication Data
US 2020/0360568 A1 Nov. 19, 2020

(30) Foreign Application Priority Data
Sep. 30, 2016 (JP) .............................. JP2016-193920

(51) Int. Cl.
| B05D 1/00 | (2006.01) |
| B05D 7/24 | (2006.01) |
| A61L 27/44 | (2006.01) |
| A61C 8/02 | (2006.01) |
| A61F 2/28 | (2006.01) |
| A61L 27/54 | (2006.01) |
| A61L 27/56 | (2006.01) |
| A61L 27/58 | (2006.01) |

(52) U.S. Cl.
CPC ............ *A61L 27/44* (2013.01); *A61C 8/0006* (2013.01); *A61F 2/2846* (2013.01); *A61L 27/54* (2013.01); *A61L 27/56* (2013.01); *A61L 27/58* (2013.01); *B05D 1/005* (2013.01); *B05D 7/24* (2013.01); *A61F 2250/0024* (2013.01); *A61L 2400/18* (2013.01); *A61L 2430/02* (2013.01); *A61L 2430/12* (2013.01)

(58) Field of Classification Search
CPC ......... B05D 1/005; A61L 27/44; A61L 27/54; A61L 27/56; A61L 27/58; A61L 2400/18; A61L 2430/02; A61L 2430/12; A61C 8/0006; A61F 2/2846; A61F 2250/0024
See application file for complete search history.

(56) References Cited

U.S. PATENT DOCUMENTS

| 6,514,286 B1 * | 2/2003 | Leatherbury ........... A61L 27/12 623/11.11 |
| 2011/0045047 A1 | 2/2011 | Bennett et al. |
| 2011/0070288 A1 * | 3/2011 | Andjelic ........... A61F 13/00029 424/445 |
| 2012/0010636 A1 | 1/2012 | Boey et al. |
| 2012/0251752 A1 | 10/2012 | Hayashi et al. |

FOREIGN PATENT DOCUMENTS

| CN | 101954126 | | 1/2011 | |
| CN | 101954126 A | * | 1/2011 | ............. A61L 27/56 |
| DE | 10108545 A1 | * | 9/2002 | ............. B82Y 40/00 |
| JP | H4-135483 | | 5/1992 | |
| JP | H08-325521 | | 12/1996 | |
| JP | 2002-085547 | | 3/2002 | |
| JP | 2004-322535 | | 11/2004 | |
| JP | 2008-536699 | | 9/2008 | |
| JP | 2011-139898 | | 7/2011 | |
| JP | 2012-095731 | | 5/2012 | |
| JP | 2012-096038 | | 5/2012 | |
| JP | 2012095731 A | * | 5/2012 | |
| JP | 2012-517319 | | 8/2012 | |
| JP | 2013-505109 | | 2/2013 | |
| KR | 10-1554490 | | 9/2015 | |

OTHER PUBLICATIONS

Vendra, V. K.; Wu, L.; Krishnan, S. In Nanomaterials for the Life Sciences vol. 5: Nanostructured Thin Films and Surfaces; Kumar, C. S. S. R., Ed.; WILEY-VCH: Weinheim, 2010; pp. 1-54. (Year: 2010).*
"Spin Coating Theory," https://www.spincoating.com/en/applications/spin-coating-theory-process/68/, May 13, 2016, Retrieved from https://web.archive.org/web/20160513144209/https://www.spincoating.com/en/applications/spin-coating-theory-process/68/on Feb. 12, 2021. (Year: 2016).*
"dense, adj." OED Online, Oxford University Press, Dec. 2020, oed.com/view/Entry/50026. Accessed Feb. 12, 2021. (Year: 2020).*
International Search Report for PCT/JP2017/020592 dated Sep. 5, 2017.
Gisaku Takahashi, "Review of Polymer Films, Polymers," vol. 13, No. 2, p. 100-107 (1964), Sep. 21, 2011, With Partial Translation.
Akihiro Kitamura et al., "Asymptotic Analysis of Thin-Film Formation during Spin Coating," Nagare; vol. 19, No. 1, p. 27-36 (2000), Jan. 13, 2000, With English Abstract.

* cited by examiner

*Primary Examiner* — William P Fletcher, III
(74) *Attorney, Agent, or Firm* — IPUSA, PLLC

(57) ABSTRACT

A method of producing a bioabsorbable membrane includes: forming a liquid membrane by spin-coating a coating liquid containing a first bioabsorbable polymer and a solvent; and forming a dense layer by causing a porous membrane containing a second bioabsorbable polymer to contact the liquid membrane.

2 Claims, 1 Drawing Sheet

METHOD OF PRODUCING BIOABSORBABLE MEMBRANE

TECHNICAL FIELD

The present invention relates to a method of producing bioabsorbable membrane and a bioabsorbable membrane.

BACKGROUND ART

In fields such as a medical field and a dental field, bioabsorbable membranes are used in order to regenerate periodontal tissues, bone tissues, and the like (see, for example, Patent Document 1). Bioabsorbable membranes are used, for example, as GTR (guided tissue regeneration) membranes and GBR (guided born regeneration) membranes.

A bioabsorbable membrane has a bioabsorbable polymer as a basic component, and is used to induce tissue regeneration by physically isolating tissues to be regenerated from the surrounding tissues, and after an elapse of a fixed time, the bioabsorbable membrane is decomposed in a living body and absorbed.

As a bioabsorbable membrane, a bioabsorbable membrane in which one surface is a dense layer and the other surface is a porous layer is known.

The porous layer serves to supply and hold blood, nutrients, and the like, and serves as a scaffold for regenerating tissues.

The dense layer serves to prevent invasion of tissues, bacteria, and the like.

Patent Document 2 discloses a porous member including a nonporous core layer and a porous surface layer and in which the core layer and the surface layer are composed of a same polymer material. Here, in the porous member, the surface layer is integrally formed on the surface of the core layer, and the porous member does not have an adhesive layer between the core layer and the surface layer.

Also, Patent Document 2 discloses a method of producing a porous member including (A) an immersing step of immersing a polymer substrate in a solvent capable of dissolving the polymer substrate and (B) a freeze-dry step of freezing-drying the immersed polymer substrate.

PRIOR ART DOCUMENTS

Patent Documents

[Patent Document 1] Japanese Laid-open Patent Publication No. 2002-85547
[Patent Document 2] Japanese Laid-open Patent Publication No. 2011-139898

DISCLOSURE OF THE INVENTION

Problem to be Solved by the Invention

However, because the thicknesses of the core layer and the surface layer are not easily controlled, the thickness of the core layer could not be made uniform.

An object in one aspect of the present invention is to provide a bioabsorbable membrane in which a dense layer having a uniform thickness is formed with a porous layer.

Means for Solving the Problem

According to one aspect of the present invention, a method of producing a bioabsorbable membrane includes: forming a liquid membrane by spin-coating a coating liquid containing a first bioabsorbable polymer and a solvent; and foaming a dense layer by causing a porous membrane containing a second bioabsorbable polymer to contact the liquid membrane.

According to another aspect of the present invention, a bioabsorbable membrane includes: a dense layer containing a first bioabsorbable polymer; and a porous membrane containing a second bioabsorbable polymer, wherein the dense layer has an average thickness of 10 μm or more and 500 μm or less, and a percentage of an average deviation of thicknesses to the average thickness is 20% or less.

Effects of the Invention

According to one aspect of the present invention, it is possible to provide a bioabsorbable membrane in which a dense layer having a uniform thickness is formed with a porous layer.

EMBODIMENT FOR CARRYING OUT THE INVENTION

Next, an embodiment for carrying out the present invention will be described.

[Bioabsorbable Membrane]

Figure 1:
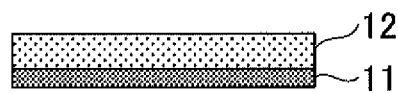
FIG. 1 is a diagram illustrating an example of a bioabsorbable membrane of the present embodiment.

FIG. 1 illustrates an example of a bioabsorbable membrane of the present embodiment.

A bioabsorbable membrane 10 includes a dense layer 11 containing a first bioabsorbable polymer and a porous layer 12 containing a second bioabsorbable polymer.

The bioabsorbable polymers are not particularly limited. As the bioabsorbable polymers, for example, a homopolymer or a copolymer of glycolic acid, lactic acid, dioxanone, β-hydroxybutyl carboxylic acid, β-propiolactone, γ-butyrolactone, γ-valero-3 methylbutyrolactone, δ-valerolactone, ε-caprolactone, ethylene glycol, or trimethylene carbonate, or two or more kinds of these may be used in combination.

In consideration of the adhesiveness between the dense layer 11 and the porous layer 12, the first bioabsorbable polymer and the second bioabsorbable polymer may be the same, but the dense layer 11 and the porous layer may differ from each other when the adhesiveness between the dense layer 11 and the porous layer 12 is favorable.

The average thickness of the dense layer 11 is 10 μm or more and 500 μm or less, and is preferably 30 μm or more and 200 μm or less. By setting the average thickness of the dense layer 11 to 10 μm or more and 500 μm or less, it is possible to adequately secure the period of time for the bioabsorbable membrane 10 to be absorbed in a living body.

The percentage of the average deviation of thicknesses to the average thickness of the dense layer 11 is 20% or less, and is preferably 10% or less. By setting the percentage of the average deviation of thicknesses to the average thickness of the dense layer 11 to 20% or less, the characteristics of the bioabsorbable membrane 10 can be made uniform, and as a result, the operability when the bioabsorbable membrane 10 is implanted in a body is enhanced.

The bioabsorbable membrane 10 can be used, for example, as an antiadhesive material, a GTR (guided tissue regeneration) membrane, a GBR (guided born regeneration) membrane, or the like.

[Method of Producing Bioabsorbable Membrane]

Figure 2A:
FIG. 2A is a diagram illustrating an example of a method of producing the bioabsorbable membrane.
Figure 2B:
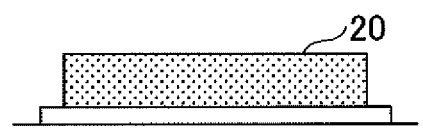
FIG. 2B is a diagram illustrating an example of a method of producing the bioabsorbable membrane.
Figure 2C:
FIG. 2C is a diagram illustrating an example of a method of producing the bioabsorbable membrane.

FIGS. 2A to 2C illustrate an example of a method of producing the bioabsorbable membrane 10.

First, a coating liquid containing the first bioabsorbable polymer and a solvent is spin-coated to form a liquid membrane L (see FIG. 2A). Next, while causing the porous membrane 20 to contact the liquid membrane L or after causing the porous membrane 20 to contact the liquid membrane L (see FIG. 2B), by drying, the dense layer 11 is formed (see FIG. 2C). Therefore, the bioabsorbable membrane 10 in which the dense layer 11 having a uniform thickness is formed with the porous layer 12 can be produced.

The solvent is not particularly limited as long as it is able to dissolve or disperse a bioabsorbable polymer. As the solvent, for example, dichloromethane, chloroform, THF, 1,4-dioxane, water, acetonitrile, acetone, benzene, or the like may be used, and two or more kinds of these may be used in combination.

The content of the first bioabsorbable polymer in the coating liquid is preferably 0.3% by mass or more and 20% by mass or less, and is more preferably 0.5% by mass or more and 10% by mass or less. When the content of the first bioabsorbable polymer in the coating liquid is 0.3% by mass or more, volatilization of the solvent in the coating liquid can be suppressed, and when the content of the first bioabsorbable polymer in the coating liquid is 20% by mass or less, the coating liquid can be easy to be spin-coated uniformly.

The coating liquid may further contain another substance. For example, when the coating liquid further contains a physiologically active substance, the bioabsorbable membrane 10 can have a sustained release ability of the physiologically active substance. It is preferable that the liquid membrane L is formed by, after placing the coating liquid on a substrate fixed to a rotating base, rotating the rotating base.

At this time, the thickness of the liquid membrane L can be uniformly controlled by controlling the content of the first bioabsorbable polymer in the coating liquid, the placing amount of the coating liquid, and the rotation speed of the rotating base.

The substrate may be a flat plate, or protrusions-recesses such as a texture, a pattern, a design, a character, or a symbol may be provided on the surface of the substrate. When protrusions-recesses or the like are provided on the surface of the substrate, protrusions-recesses or the like can be provided on the surface of the dense layer 11. This makes it easy to recognize, for example, the front and back of the bioabsorbable membrane 10, and information on a producer or the like can be added to the bioabsorbable membrane 10.

Also, by providing protrusions-recesses or the like on the surface of the dense layer 11, the surface shape and the surface roughness of the dense layer 11 can be changed. This may change the response of cells and the like when the bioabsorbable membrane 10 is implanted in a living body and may control curative effects to be further enhanced.

Although a material constituting the substrate is not particularly limited, stainless steel, Ti, or the like can be used as the material constituting the substrate.

It is preferable that a release layer is formed on the surface of the substrate.

Although a material constituting the release layer is not particularly limited, diamond-like carbon (DLC) or the like can be used as the material constituting the release layer.

When spin-coating the coating liquid, it is preferably that after the rotating base is rotated at 50 rpm or more and 500 rpm or less for a preliminary rotation, the rotating base is rotated at 500 rpm or more and 3000 rpm or less for a main rotation. As a result, stretching unevenness of the liquid membrane L can be suppressed, and the thickness of the dense layer 11 can be made further uniform.

The average thickness of the porous membrane 20 is preferably 100 μm or more and 1000 μm or less, and is more preferably 100 μm or more and 300 μm or less. By setting the average thickness of the porous membrane 20 to 100 μm or more and 1000 μm or less, it is possible to adequately secure the period of time for the bioabsorbable membrane 10 to be absorbed in a living body.

The percentage of the average deviation of thicknesses to the average thickness of the porous membrane 20 is preferably 20% or less, and is more preferably 10% or less. By setting the percentage of the average deviation of thicknesses to the average thickness of the porous membrane 20 to 20% or less, the characteristics of the bioabsorbable membrane 10 can be made uniform, and as a result, the operability when the bioabsorbable membrane 10 is implanted in a body is enhanced.

The average pore size of the porous membrane 20 is preferably 0.2 pin or more and 500 μm or less, and is more preferably 20 μm or more and 300 μm or less. By setting the average pore size of the porous membrane 20 to 0.2 μm or more, it is possible to ensure a body fluid permeability of the bioabsorbable membrane 10, and by setting the average pore diameter of the porous membrane 20 to 500 μm or less, it is possible to secure a clot retention property of the bioabsorbable membrane 10. The porosity rate of the porous membrane 20 is preferably 30% or more and 99% or less, and is more preferably 75% or more and 90% or less. By setting the porosity rate of the porous membrane 20 to 30% or more, it is possible to ensure a body fluid permeability of the bioabsorbable membrane 10, and by setting the porosity rate of the porous membrane 20 to 99% or less, it is possible to ensure strength of the bioabsorbable membrane 10.

The porous membrane 20 can be produced by a known method (see, for example, Patent Document 1).

Note that as the porous membrane 20, a commercially available product, which is a commercially available porous membrane, having a uniform thickness may be used.

According to the present embodiment, while causing the porous membrane 20 to contact the liquid membrane L or after causing the porous membrane 20 to contact the liquid membrane L, by drying, the dense layer 11 including the first bioabsorbable polymer is formed.

At this time, by causing the porous membrane 20 to contact the liquid membrane L, a part of the liquid membrane L permeates into the porous membrane 20. By drying in this state, the solvent contained in the liquid membrane L volatilizes, and the first bioabsorbable polymer derived from the liquid membrane L and the second bioabsorbable polymer derived from the porous membrane 20 are integrated. Thereby, the bioabsorbable membrane 10 including the dense layer 11 and the porous layer 12 is formed.

Although the drying method is not particularly limited as long as it does not degenerate bioabsorbable polymers, a vacuum drying method or the like may be used as the drying method.

Finally, the bioabsorbable membrane 10 is peeled from the substrate. At this time, for example, when ethanol or an ethanol aqueous solution is applied to the interface between the substrate and the bioabsorbable membrane 10, the bioabsorbable membrane 10 is easily peeled. Also, when protrusions-recesses or the like are provided on the surface of the substrate, the bioabsorbable membrane 10 is easily peeled off.

EXAMPLES

In the following, although the present invention will be described in more details with reference to Examples, the present invention is not limited to Examples.

Example 1

In 93 parts by mass of 1,4-dioxane, 7 parts by mass of poly-DL-lactic acid (PDLLA) were dissolved to obtain a coating liquid.

As a substrate, a SUS 304 plate (104 mm×84 mm×2 mm) having a DLC membrane formed thereon was used.

As a porous membrane, a sponge (70 mm×80 mm) made of PDLLA having an average pore size of 121 μm and a porosity rate of 81% was used.

10 locations of the porous membrane were cut out. Next, using a p focus X-ray CT system inspeXio SMX-100CT (manufactured by Shimadzu Corporation), the porous membrane was photographed under conditions of a tube voltage of 55 kV, a tube current of 40 μA, and a strong enlargement of voxel size of 3 μm. Three-dimensional images were acquired from the obtained data, and it was confirmed that it was a porous membrane.

Also, tomographic images (CT images) orthogonal to the porous membrane were acquired, and the thicknesses of the porous membrane were measured using image processing software ImageJ. At this time, for three points from each CT image, the thicknesses were measured at 30 points. As a result, an average thickness of the porous membrane was 500 μm and an average deviation of thicknesses of the porous membrane was 32 μm.

After fixing the substrate on a rotating base of a spin coater MS-B100 (manufactured by Mikasa Corporation), 4.5 mL of the coating liquid was placed on the substrate. Next, after the rotating base was rotated at 300 rpm for 3 seconds as a preliminary rotation, the rotating base was rotated at 2000 rpm for 3 seconds as a main rotation to form a liquid membrane. After stopping the rotation of the rotating base, the porous membrane was immediately placed on the liquid membrane and then vacuum-dried at an ambient temperature for 2.5 hours to form a dense layer to, prepare a bioabsorbable membrane. Finally, an 80% ethanol aqueous solution was sprayed onto the interface between the substrate and the bioabsorbable membrane, and the bioabsorbable membrane was peeled from the substrate.

Note that all of the above steps were carried out in an environment of an ambient temperature (23° C.)

Ten locations of the obtained bioabsorbable membrane were cut out. Next, using a p focus X-ray CT system inspeXio SMX-100CT (manufactured by Shimadzu Corporation), the bioabsorbable membrane was photographed under conditions of a tube voltage of 55 kV, a tube current of 40 μA, and a strong enlargement of voxel size of 3 μm. From the obtained data, three-dimensional images were acquired and it was confirmed that it was composed of a dense layer and a porous layer.

Also, tomographic images (CT images) orthogonal to the porous membrane were acquired, and the thicknesses of the porous membrane were measured using image processing software ImageJ. At this time, for three points from each CT image, the thicknesses were measured at 30 points. As a result, an average thickness of the dense layer was 98 μm and an average deviation of thicknesses of the dense layer was 12 μm.

Example 2

With the exception of setting the rotation speed in a main rotation to 500 rpm, a bioabsorbable membrane was prepared under the same conditions as in Example 1. The obtained bioabsorbable membrane was composed of a dense layer and a porous layer, an average thickness of the dense layer was 152 μm, and an average deviation of thicknesses of the dense layer was 19 μm.

Example 3

With the exception of setting the rotation speed in a main rotation to 3000 rpm, a bioabsorbable membrane was prepared under the same conditions as in Example 1. The obtained bioabsorbable membrane was composed of a dense layer and a porous layer, an average thickness of the dense layer was 51 μm, and an average deviation of thicknesses of the dense layer was 6 μm.

Table 1 indicates the characteristics of the porous membranes, and the dense layers of the bioabsorbable membranes of Examples 1 to 3.

TABLE 1

| | POROUS MEMBRANE | | | DENSE LAYER | | |
|---|---|---|---|---|---|---|
| | AVERAGE THICKNESS $T_0$ [μm] | AVERAGE DEVIATION OF THICKNESSES $D_0$ [μm] | $D_0/T_0$ [%] | AVERAGE THICKNESS $T_1$ [μm] | AVERAGE DEVIATION OF THICKNESSES $D_1$ [μm] | $D_1/T_1$ [%] |
| Example 1 | 500 | 32 | 6.4 | 98 | 12 | 12.2 |
| Example 2 | 500 | 32 | 6.4 | 152 | 19 | 12.5 |
| Example 3 | 500 | 32 | 6.4 | 51 | 6 | 11.8 |

It can be seen from Table 1 that in each of the bioabsorbable membranes of Examples 1 to 3, the thickness of the dense layer is uniform.

The present international application is based on and claims priority to Japanese Patent Application No. 2016-193920, filed on Sep. 30, 2016, the entire contents of Japanese Patent Application No. 2016-193920 are hereby incorporated herein by reference.

DESCRIPTION OF REFERENCE SYMBOLS

10 bioabsorbable membrane
11 dense layer
12 porous layer
20 porous membrane
L liquid membrane

The invention claimed is:
1. A method of producing a bioabsorbable membrane including a first layer containing a first bioabsorbable polymer and a porous layer containing a second bioabsorbable polymer, the method comprising:
   forming a liquid membrane by spin-coating a coating liquid containing the first bioabsorbable polymer and a solvent; and after forming the liquid membrane, forming the first layer and the porous layer by causing a porous membrane containing the second bioabsorbable polymer to contact the liquid membrane such that a part of the liquid membrane permeates into the porous membrane and by evaporating the solvent contained in the liquid membrane by drying.

2. The method of producing the bioabsorbable membrane according to claim 1, wherein when spin-coating the coating liquid, after a rotating base to which the coating liquid is applied is rotated at 50-500 rpm for a preliminary rotation, the rotating base is rotated at 500-3000 rpm for a main rotation.

\* \* \* \* \*